United States Patent
Shore et al.

(10) Patent No.: US 7,901,940 B2
(45) Date of Patent: Mar. 8, 2011

(54) METHOD FOR MEASURING RECOVERY OF CATALYTIC ELEMENTS FROM FUEL CELLS

(75) Inventors: Lawrence Shore, Edison, NJ (US); Ramail Matlin, Berkeley, NJ (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 12/134,543

(22) Filed: Jun. 6, 2008

(65) Prior Publication Data
US 2009/0301171 A1 Dec. 10, 2009

(51) Int. Cl.
G01N 33/20 (2006.01)

(52) U.S. Cl. .............. 436/37; 436/79; 436/80; 436/84; 436/166; 436/172; 436/173; 436/174; 356/316; 356/318; 250/288

(58) Field of Classification Search ............ 436/37, 436/73, 80, 84
See application file for complete search history.

(56) References Cited

U.S. PATENT DOCUMENTS

| | | | | |
|---|---|---|---|---|
| 3,901,599 | A * | 8/1975 | Meric | 356/318 |
| 6,002,478 | A * | 12/1999 | Zhu | 356/316 |
| 7,544,232 | B2 * | 6/2009 | Hackl et al. | 75/744 |
| 2002/0030076 | A1 * | 3/2002 | Gay et al. | 226/7 |
| 2004/0028179 | A1 | 2/2004 | Rosso et al. | |
| 2004/0146434 | A1 | 7/2004 | Kane et al. | |
| 2004/0237721 | A1 * | 12/2004 | Baghalha | 75/744 |
| 2008/0090295 | A1 * | 4/2008 | Feuerstein et al. | 436/54 |

FOREIGN PATENT DOCUMENTS

| | | |
|---|---|---|
| JP | 20030247920 A | 9/2003 |
| JP | 20050024332 A | 1/2005 |

OTHER PUBLICATIONS

McCandless, Tom E.; Baker, Mark E.; and Ruiz, Joaquin. "Trace element analysis of natural gold by laser ablation ICP-MS: a combined external/internal standardisation approach," Geostandards Newsletter, 1997 21.2 271-278.*

Figueiredo, A. M. G. et al. "NAA and UV laser ablation ICP-MS for platinum group elements and gold determination in NiS fire assay buttons," J. Radioanalytical and Nuclear Chem., 2000 244.3 623-625.*

(Continued)

*Primary Examiner* — Yelena G Gakh
*Assistant Examiner* — Christopher A. Hixson
(74) *Attorney, Agent, or Firm* — Bernard Lau (57) ABSTRACT

A method is provided for measuring the concentration of a catalytic element in a fuel cell powder. The method includes depositing on a porous substrate at least one layer of a powder mixture comprising the fuel cell powder and an internal standard material, ablating a sample of the powder mixture using a laser, and vaporizing the sample using an inductively coupled plasma. A normalized concentration of catalytic element in the sample is determined by quantifying the intensity of a first signal correlated to the amount of catalytic element in the sample, quantifying the intensity of a second signal correlated to the amount of internal standard material in the sample, and using a ratio of the first signal intensity to the second signal intensity to cancel out the effects of sample size.

21 Claims, 7 Drawing Sheets

OTHER PUBLICATIONS

Zhang, Yuefei et al. "Determination of trace rare earth elements in coal fly ash and atmospheric particules by electrothermal vaporization inductively coupled plasma mass spectrometry with slurry sampling," Environmental Pollution, Jul. 2007 148 459-467.*

Westheide, Jochen Th. et al. "Analysis of ceramic layers for solid oxide fuel cells by laser ablation inductively coupled plasma mass spectroscopy," J. Anal. Atomic Spectrom. 1996 11 661-666.*

Rauch, Sebastien et al. "Scanning laser ablation-ICP-MS tracking of platinum group elements in urban particles," Sci. of the Total Env. 2002 286 243-251.*

Odegard, Magne. "Preparation of synthetic calibration materials for use in the microanalysis of oxide minerals by direct fusion in high-purity graphite electrodes: preliminary results for quartz and rutile," Geostandards Newsletter 1999 23 173-186.*

Wolthers, M. et al. "Arsenic uptake by pyrite at ambient environmental conditions: a continuous-flow experiment," appeared in Advances in Arsenic Research, Chapter 5, Oct. 2005, ACS Symposium Series v. 915, ACS, p. 60-76.*

Pisonero, Jorge et al. "Laser ablation inductively coupled plasma mass spectrometry for direct analysis of the spatial distribution of trace elements in metallurgical-grade silicon," Anal. Bioanal. Chem. Aug. 12, 2006 386 12-20.*

Ludke, C. et al. "Comparative studies on metal determination in airborne particulates by LA-ICP-MS and furnace atomization non-thermal excitation spectrometry," Fresenius J. Anal. Chem. 1994 350 272-276.*

Tyler, Geoffrey. "ICP-MS, or ICP-AES and AAS?—a comparison." Varian Inc brochure, Apr. 1994.*

Guerleyuek, Hakan et al. "Determination of extractable arsenic in soils using slurry sampling-on-line microwave extraction-hydride generation-atomic absorption spectrometry." Spectrochimica Acta Part B (2000) 55 935-942.*

Jdid, E. A. et al. "Acid and oxidizing leaching of copper refinery anodic slimes in hexafluorosilicic acid and nitric acid media." Separation Science and Technology (1996) 31 569-577.*

Lee, Cin-Ty A. "Laser ablation ICP-MS: Data reduction." Accessed online at <http://www.ruf.rice.edu/~ctlee/LASERABLATIONICP.pdf> on May 24, 2010. Published Sep. 24, 2006.*

Kanicky, Viktor et al. "Use of internal standardization to compensate for a wide range of absorbance in the analysis of glasses by UV laser ablation inductively coupled plasma atomic emission spectroscopy." Applied Spectroscopy (1998) 52 638-642.*

Klemm, W. et al. "A simple method of target preparation for the bulk analysis of powder samples by laser ablation inductively coupled plasma mass spectrometry (LA-ICP-MS)." Fresnius Journal of Analytical Chemistry (2001) 370 641-646.*

Outokumpu Technology Product Brochure. "Slurry Sampling." Published in Helsenki, Finland Jul. 2006. Accessed online at <http://www.outotec.com/35365.epibrw> on May 24, 2010.*

U.S. Appl. No. 11/844,723, Shore et al.

J. E. Barnes and J. D. Edwards, "Solvent Extraction at INCO's Acton Precious Metal Refinery," *Chemistry and Industry,* Mar. 6, 1982, 151-155.

M. Alkan, et al, "Solubility of Chlorine in Aqueous Hydrochloric Acid Solutions," *Journal of Hazardous Materials,* vol. 119, Issues 1-3, Mar. 17, 2005, p. 13-18.

Shore L: "Platinum Group Metal Recycling Technology Development" Jun. 11, 2008, DOE Hydrogen Program Annual Merit Review and Peer Evaluation Meating, Washington DC., pp. 1-32, XP002547123 the whole document.

Shore L: "Platinum Group Metal Recycling Technology Development" DOE Hydrogen Program: Annual Progress Report, Washington DC, Nov. 1, 2007, pp. 1027-1030, XP002502884 p. 1028-1029.

Potts P.J., Bowles, J.F.W., Reed, S.J.B., Cave, M.R.: "Microprobe techniques in the earth sciences" 1995, Springer, London, XP008113212 paragraphs [07.3]-[07.5].

* cited by examiner

METHOD FOR MEASURING RECOVERY OF CATALYTIC ELEMENTS FROM FUEL CELLS

GOVERNMENT SUPPORT

The work described herein was supported, in part, by grant DE-FC36-03GO13104 from the United States Department of Energy. Therefore, the U.S. Government may have certain rights in this invention.

BACKGROUND OF THE INVENTION

Fuel Cells are devices that release electrical energy using an electrochemical reaction. A major class of fuel cells utilizes hydrogen fuel, and the electrochemical oxidation of hydrogen to water is catalyzed using electrodes containing precious metal catalysts. Precious metal catalytic elements for use in precious metal catalysts include, but are not limited to, platinum (Pt), ruthenium (Ru), palladium (Pd), gold (Au), and rhodium (Rh). It is widely accepted that the high cost and limited supply of platinum and other catalytic elements are obstacles to large scale commercialization of fuel cells.

There are several types of fuel cells. Most common is the polymer electrolyte membrane (PEM) fuel cell. The PEM forms the basis for a membrane electrode assembly (MEA), which is the structure by which hydrogen can be oxidized to generate electricity. An anode (i.e., a negative electrode) is provided on one side of the PEM and a cathode (i.e., a positive electrode) is provided on the opposite side of the PEM. The anode contains a catalyst, typically comprising platinum, for promoting dissociation of hydrogen into electrons and positive hydrogen ions. The cathode also contains a catalyst, typically comprising platinum, for promoting reduction of oxygen. An MEA typically carries a catalytic element loading between about 0.5 mg/cm$^2$ and 4 mg/cm$^2$, although recent research has obtained effective performance with catalytic element loadings as low as 0.15 mg/cm$^2$. Typically, these loadings in current commercial fuel cells translate to about 0.5% to 2.0% by weight of catalytic element in the MEA.

A commonly used polymer electrode membrane is Nafion™ by E.I. DuPont de Nemours Company. Nafion™, a Teflon™-based polymer, is a sulfonated perfluropolymer. Even when using a membrane that is itself free of fluorine, a perfluropolymer ionomer is typically mixed into the electrocatalyst layers (i.e., the anion and the cation) to improve the mobility of the positive hydrogen ions. Additionally, the presence of a fluoride-rich polymer tends to make the powder of the MEA hydrophobic when the MEA is ground.

In some PEM fuel cells, a carbonaceous gas diffusion layer is applied to the anode and another carbonaceous gas diffusion layer is applied to the cathode to form a catalyst coated membrane (CCM). The gas diffusion layers provide for the uniform distribution of hydrogen and oxygen to their respective sides of the PEM, provide a conductive pathway for electricity to be transmitted out of the fuel cell, and provide a porous structure for the water produced by the electrochemical reaction to be transported away.

Other types of fuel cells also utilize catalytic elements such as platinum, including alkaline fuel cells (AFC) and phosphoric acid fuel cells (PAFC). After a period of use, a fuel cell often must be replaced, because of fouling of the catalyst, or for another reason. Due to the value of the precious metal catalyst, it is highly desirable to recover as much precious metal as possible from the MEA.

The conventional approach to recover of platinum and other precious metal catalytic elements from an MEA includes combusting the PEM and the carbonaceous diffusion layers, dissolving the resultant ash in acid, and purifying the precious metal using standard refining chemistry. However, the high fluorine content of the MEA, particularly those with Nafion™ or other Teflon™-based membranes, results in toxic emissions of hydrogen fluoride gas (HF) and other fluorine compounds (e.g., carbonyl fluoride or $COF_2$) from the combustion process.

SUMMARY OF THE INVENTION

A method is provided for measuring the concentration of a catalytic element in a fuel cell powder. The method includes depositing on a porous substrate at least one layer of a powder mixture comprising the fuel cell powder and an internal standard material, ablating a sample of the powder mixture using a laser, and vaporizing the sample using an inductively coupled plasma. The method further includes quantifying the intensity of a first signal correlated to the concentration of catalytic element in the sample, quantifying the intensity of a second signal correlated to the concentration of internal standard material in the sample, and calculating a normalized concentration of catalytic element in the sample based on the ratio of the first signal intensity to the second signal intensity.

The step of depositing a layer of powder mixture on a porous substrate can include forming a first slurry comprising the fuel cell powder, forming a second slurry comprising the internal standard material, mixing the first slurry and the second slurry into a substantially uniform slurry mixture having a liquid portion and a solids portion, and exposing the slurry mixture to the porous substrate so that the liquid portion passes through the porous substrate and the solids portion is deposited on the porous substrate to form the layer of powder mixture.

A method is provided for measuring the recovery of a catalytic element from a fuel cell membrane electrode assembly powder. The method includes depositing on a porous substrate a layer of a first powder mixture comprising the fuel cell powder, ablating a first sample of the first powder mixture using a laser, vaporizing the first sample using an inductively coupled plasma, and quantifying the concentration of catalytic element in the first sample. After extracting at least a portion of the catalytic element from the fuel cell powder to create a depleted fuel cell powder, the method further comprises depositing on a porous substrate a layer of a second powder mixture comprising the depleted fuel cell powder, ablating a second sample of the second powder mixture using a laser, vaporizing the second sample using an inductively coupled plasma, and quantifying the concentration of catalytic element in the second sample.

DESCRIPTION OF THE INVENTION

As used herein the term "catalytic element" is understood to include platinum or other precious metal catalytic material such as ruthenium, palladium, gold, and rhodium. Although the term "platinum" is often used interchangeably with the term "catalytic element," and platinum is frequently discussed as an exemplary catalytic element, it is understood that the methods described herein are equally applicable to other precious metal catalytic elements, including but not limited to ruthenium, palladium, gold, and rhodium.

As an alternative to the conventional approach of combusting a fuel cell membrane electrode assembly, a catalytic element can be extracted and recovered from an MEA by: (a) grinding the MEA into a powder, (b) optionally wetting the powder with a surfactant, (c) extracting catalytic element from the powder using an acid leachate, (d) separating the solids from the liquid of the resultant leachate and powder slurry, and (e) purifying the precious metal catalytic element from the liquid using conventional refining technology. Embodiments and aspects of this process are described in detail in a commonly owned U.S. patent application Ser. No. 12/134,394 entitled "Method and Apparatus for Recovering Catalytic Elements from Fuel Cell Membrane Electrode Assemblies," filed concurrently with the present application on Jun. 6, 2008. Additionally, a method of grinding the MEA into a powder using liquid nitrogen embrittlement is described in commonly owned U.S. patent application Ser. No. 11/844,723 entitled "Simplified Process for Leaching Precious Metals from Fuel Cell Membrane Electrode Assemblies," filed Aug. 24, 2007. Reagant usage and throughput can be optimized by obtaining accurate measurements of the catalytic element remaining in depleted fuel cell MEA powder after most of the catalytic element has been acid leached from the powder. The measurement methods disclosed herein are directed toward that purpose.

The process of recovering a catalytic element from the MEA results in a depleted powder having a residual amount of catalytic element. It is desirable to recover at least about 98% of the catalytic element from the MEA, so that the depleted powder preferably contains less than or equal to about 2% of the catalytic element originally in the MEA. As a starting point, an MEA typically contains about 1% by weight of catalytic element (commonly varying from about 0.5% to about 2% by weight), such that at 98% recovery, only about 200 ppm by weight of catalytic element will remain in the depleted MEA powder. To optimize the recovery of catalytic element and to verify the amount of catalytic element that has been recovered, the concentration of catalytic element remaining in the depleted powder should be measured. Preferably, the catalytic element concentration in the depleted powder can be measured in online continuous or periodic batch testing so that the process can be continually monitored and fine-tuned. Such testing is preferably performed on the depleted MEA powder, and not on the slurry comprising acid leachate and powder, because the liquid phase of the slurry contains most of the catalytic element (i.e., the catalytic element that has been extracted or leached away from the MEA powder by the acid leachate). By detecting the small residual amount of catalytic element in the depleted MEA powder, rather than the large amount of catalytic element leached into the liquid phase, the accuracy of the measurement is improved.

Figure 1:
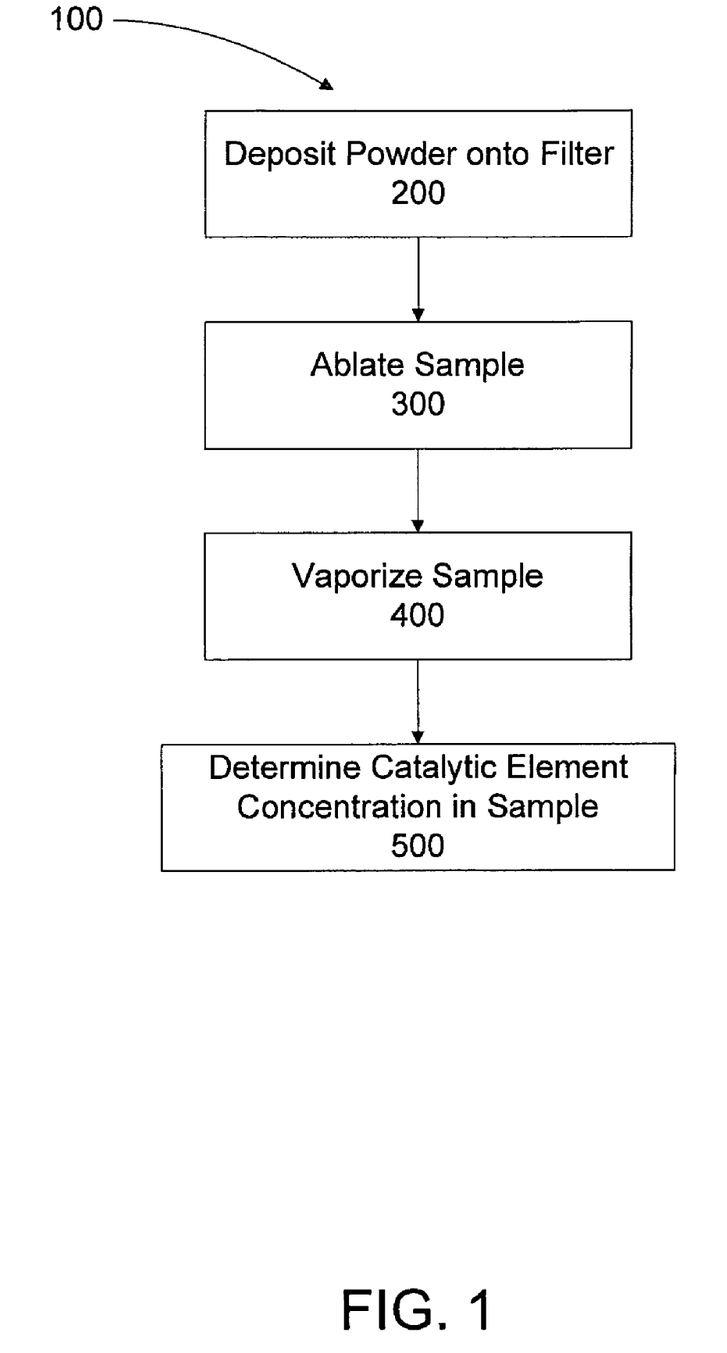
FIG. 1 is a flow chart depicting a method for measuring catalytic element concentration in a fuel cell powder.

Referring to the drawings, where like numerals identify like elements, there is shown in FIG. 1 a method 100 for measuring catalytic element concentration in a fuel cell powder. To determine the original concentration of catalytic element in the MEA powder, the fuel cell powder may comprise a powder resulting from grinding the MEA prior to catalytic element recovery. Alternatively, to determine the residual concentration of catalytic element and to verify adequate catalytic element recovery, the fuel cell powder may comprise a depleted powder that is tested after some or most of the catalytic element has been extracted. In the method of measuring catalytic element concentration depicted generally in FIG. 1, a layer of solids/powder mixture is deposited onto a porous substrate (step 200), a sample of the powder mixture is obtained using laser ablation (step 300), the sample is vaporized by an inductively coupled plasma (step 400), and the catalytic element content in the sample is quantified (step 500). The powder mixture to be measured can comprise MEA powder alone. Alternatively, the powder mixture can comprise MEA powder along with a powdered internal standard material for normalizing the catalytic element measurements by factoring out differences due to variations in sample size and uniformity of distribution of the sample.

In one embodiment of the step 200 of depositing a layer of powder mixture on a porous substrate, the porous substrate is a filter fed gravitationally from a reservoir. A slurry comprising the catalytic element containing powder is poured into the reservoir and allowed to drain through the filter, so that the liquid passes through the filter, leaving a layer of powder residue on the filter. Alternatively, a layer of powder mixture can be deposited on a porous substrate using vacuum filtration. The solids fraction of the slurry is preferably in the range of about 1% to about 10%. The slurry can be formed by wetting the powder with a surfactant. In particular, when testing the catalytic element content of the MEA powder prior to catalytic element extraction, the powder can be formed into a slurry by wetting with a surfactant and mixing with such other liquid as may be required to fluidize the powder into a slurry. The slurry can also be formed by mixing the powder with a leachate which draws catalytic element from the powder into solution, such that only a small portion of the original catalytic element remains in the powder. In particular, an acid leachate can be used to extract catalytic element from the powder, and the leachate-based slurry can be filtered to test the catalytic element content of the depleted MEA powder remaining after catalytic element extraction. Further, surfactant and leachate can be used in combination to enhance catalytic element recovery.

When the reservoir volume is large compared with the flow rate through the filter, a relatively uniform distribution coating or layer of powdered solids can be obtained on the filter. However, using too large of a reservoir volume may introduce problems due to differential settling of the MEA powder and the internal standard material. After filtering the powdered solids from the slurry, the powder can further be washed by filling the reservoir with water and allowing the water to pass through the powder and the filter. Washing allows any powder that may have settled out in the reservoir to be collected in the filter, and also provides for removal of catalytic element dissolved in the liquid phase of the slurry that is trapped within the pores and interstitial cavities of the powder, enabling the catalytic element to be collected in the filtrate. Washing is preferably done gradually to minimize disruption of the distribution of the powder residue on the filter.

Figure 2:
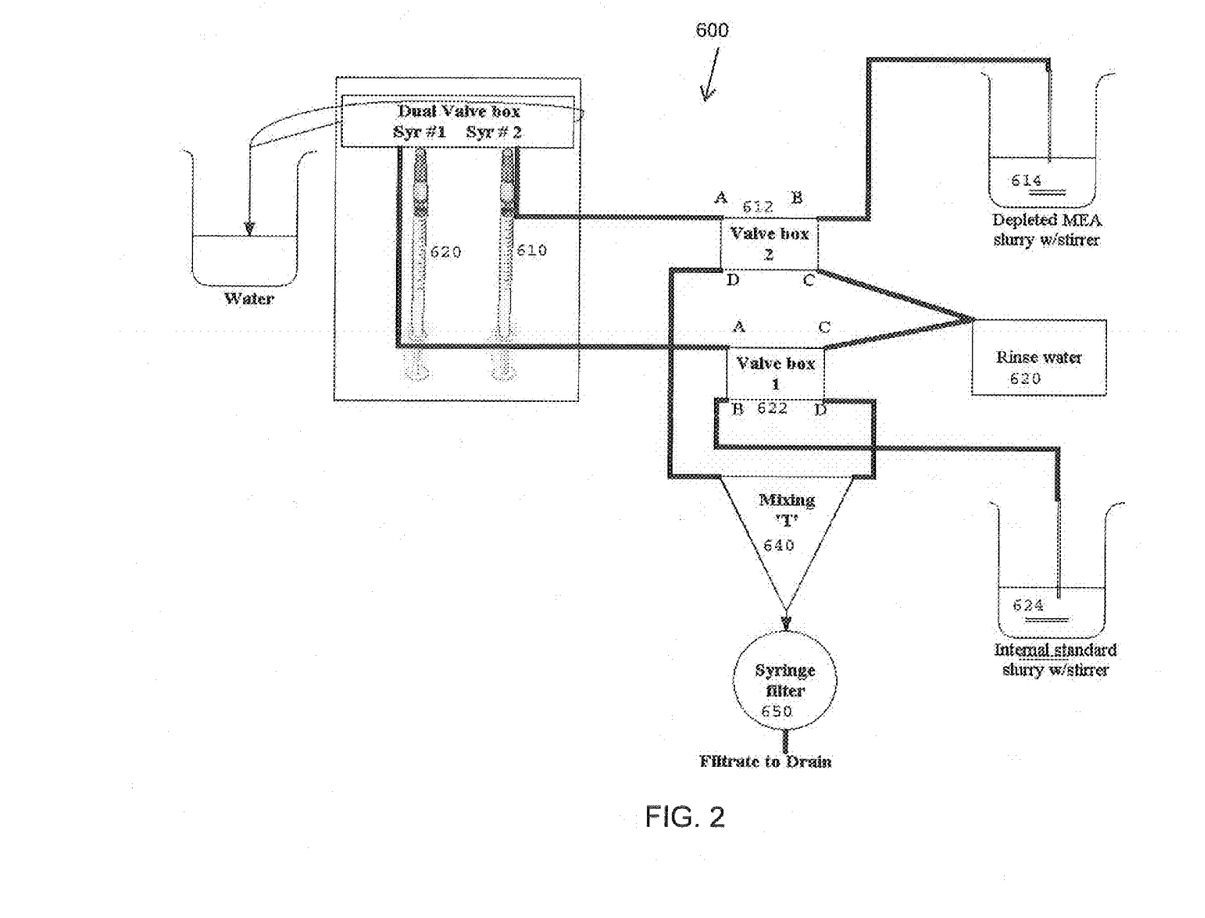
FIG. 2 is a schematic showing an apparatus for depositing a layer of powder mixture on a porous substrate.
Figure 3:
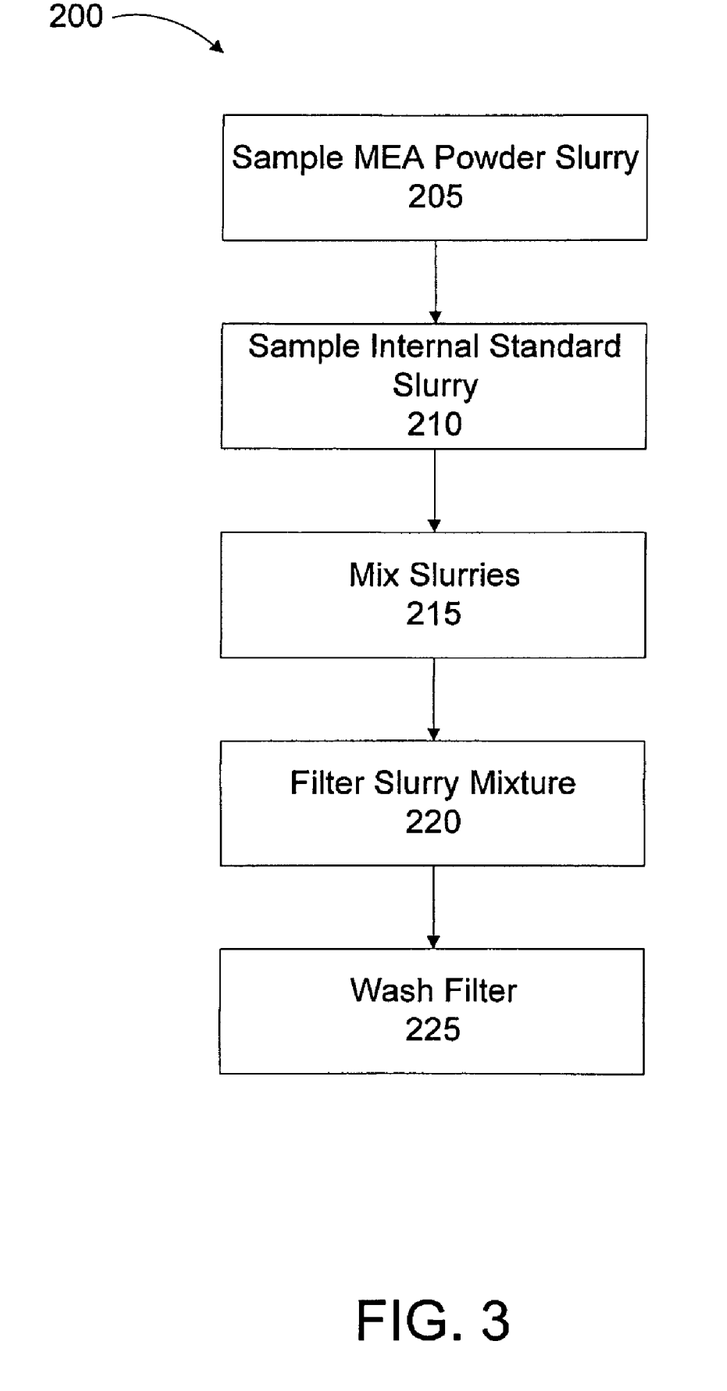
FIG. 3 is a flow chart depicting a method for depositing a layer of powder mixture on a porous substrate.
Figure 4:
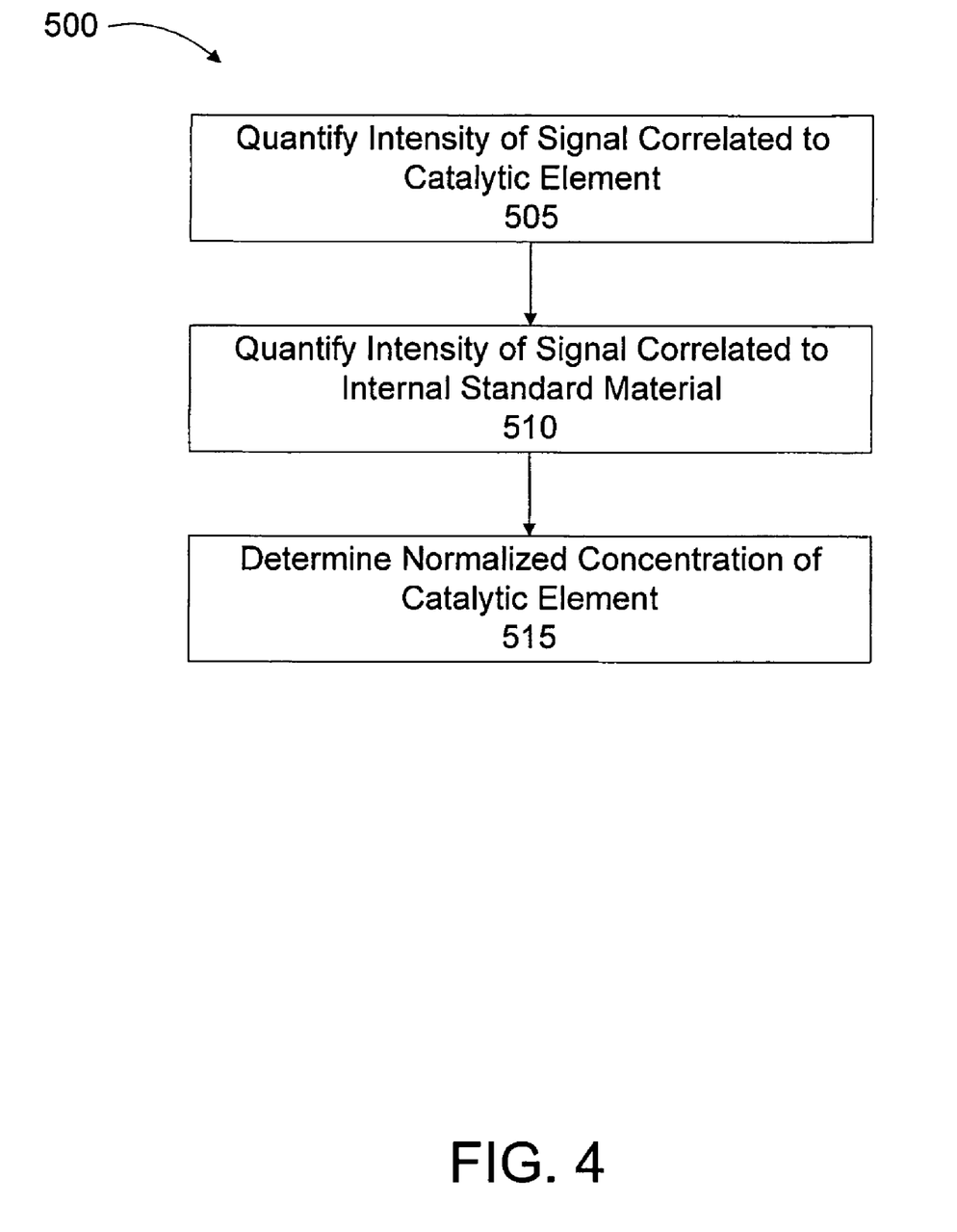
FIG. 4 is a flow chart depicting a method for quantifying catalytic element concentration in a sample of fuel cell powder.

In another embodiment of the step 200, as shown in FIG. 3, depositing a layer of powder mixture on a porous substrate can be performed using an apparatus such as that shown in FIG. 2. The tubes connecting each of the devices in the apparatus preferably have zero or very small dead volumes, and are sized to contain slurry carrying a sufficient amount of solids to be collected and sampled for measurement. In the depicted apparatus 600, the porous substrate is a filter 650. A 25 mm diameter syringe filter can be used as the filter 650 to obtain good uniformity of distribution of the layer of powder mixture. In one embodiment, the filter 650 is made from glass fibers. Alternatively, the filter 650 can be made from polysulfone, paper, fluorinated fibers, or other equivalent filtration materials. In one embodiment, the filter 650 is about 5 microns thick.

A first syringe 610 is connected to a valve 612. The valve 612 enables the syringe 610 to interconnect selectively with a reservoir 614 for holding a slurry comprising MEA powder, a reservoir 620 for holding rinse water, or a mixing valve 640. The reservoir 614 can be a reactor in which the MEA powder has been wetted by a surfactant and/or in which leachate has been used to extract catalytic element from the MEA powder. Leachate can be used to create a slurried MEA powder with or without surfactant, although testing has shown that a surfactant may increase the catalytic element recovery rate by improving mass transfer of leachate into the pores of the powder. A second syringe 620 is connected to a valve 622. The valve 622 enables the syringe 620 to interconnect selectively with a reservoir 624 for holding a slurry comprising a powdered internal standard (reference) material, the reservoir 630 for holding rinse water, or the mixing valve 640. The mixing valve 640 is adapted to combine streams of slurry from each of the first syringe 610 and the second syringe 620 to create a slurry mixture for exposing to the filter 650.

To deposit a layer of powder mixture on the filter 650, the following steps can be performed. To sample the MEA powder slurry (step 205), the syringe 610 is disposed in an empty position with the plunger fully pushed into the barrel. The valve 612 is turned to connect the syringe 610 to the reservoir 614, and slurry containing the MEA powder is drawn into the syringe 610 by pulling the plunger outwardly with respect to the barrel. To sample the internal standard material slurry (step 210), the syringe 620 is disposed in an empty position with the plunger fully pushed into the barrel. The valve 622 is turned to connect the syringe 620 to the reservoir 624, and slurry containing the internal standard material is drawn into the syringe 620 by pulling the plunger outwardly with respect to the barrel. To mix the slurries (step 215), the valves 612 and 622 are turned to connect the syringes 610 and 620, respectively, to the mixing valve 640. The syringes 610 and 620 then dispense their contents substantially simultaneously by pushing inwardly on both plungers at substantially the same time, causing the first and second slurry to be intimately and reproducibly mixed together by the mixing valve 640. To filter the slurry mixture (step 220), the resultant substantially homogenous stream of slurry is fed through the filter 650. The solids in the slurry (i.e., the remainder of the MEA powder not dissolved in the leachate or into solution) are deposited on the filter 650.

To wash the filter (step 225), the valves 612 and 622 are turned to connect the syringes 610 and 620, respectively, to the water reservoir 630, and water is drawn into the syringes 610 and 620 by pulling outwardly on their respective plungers. The valves 612 and 622 are turned to connect the syringes 610 and 620, respectively, to the mixing valve 640. The syringes 610 and 620 then dispense their contents by pushing inwardly on both plungers, causing water to flush the lines from the syringes 610 and 620, through the mixing valve 640, to the filter 650, and washing any remaining leachate and dissolved catalytic element from the pores of the depleted MEA powder. The plungers of the syringes 610 and 620 are depressed substantially simultaneously. The filter 650 can then be removed to continue the process of measuring the catalytic element concentration in the layer of solids/powder mixture that has been deposited. If desired, multiple layers of solids can be deposited on the filter 650 prior to measuring catalytic element concentration in the solids in order to increase measurement sensitivity.

Alternatively, an automated apparatus can be devised for creating a slurry mixture comprising the MEA powder with or without an internal standard material and pumping the slurry mixture through a porous substrate to filter out the solids and collect the filtrate. The slurry mixture can be created from two separate slurries, one created by automatically drawing a volume of slurry containing catalytic element from the leaching reactor, and another created by mixing a liquid with an internal standard material. The slurries can be pumped individually through a mixing valve to the porous substrate. In one embodiment, an automatic syringe dispenser, such as the ML500 series sold by the Hamilton Company, can be used to withdraw a sample mixture from the powder slurry and direct the sample to a filter whereby the solids are reproducibly deposited on a syringe filter.

To determine the completeness of leaching, i.e., to verify the amount of catalytic element that has been extracted from the MEA powder by the leachate, it would not be accurate to merely sample the catalytic element concentration in the leachate itself, because the content of catalytic element in a batch of MEA powder, and the leachability of that powder, can vary from batch to batch. Therefore, it is preferable to measure the amount of catalytic element remaining in the depleted MEA powder after each leachate extraction cycle. As described in greater detail in commonly owned copending U.S. patent application Ser. No. 12/134,394 referenced above, entitled "Method for Recovering Precious Metal Catalytic Elements from Fuel Cells," multiple leachate extraction cycles may be desirable and/or necessary to achieve an optimum catalytic element recovery rate.

Figure 5:
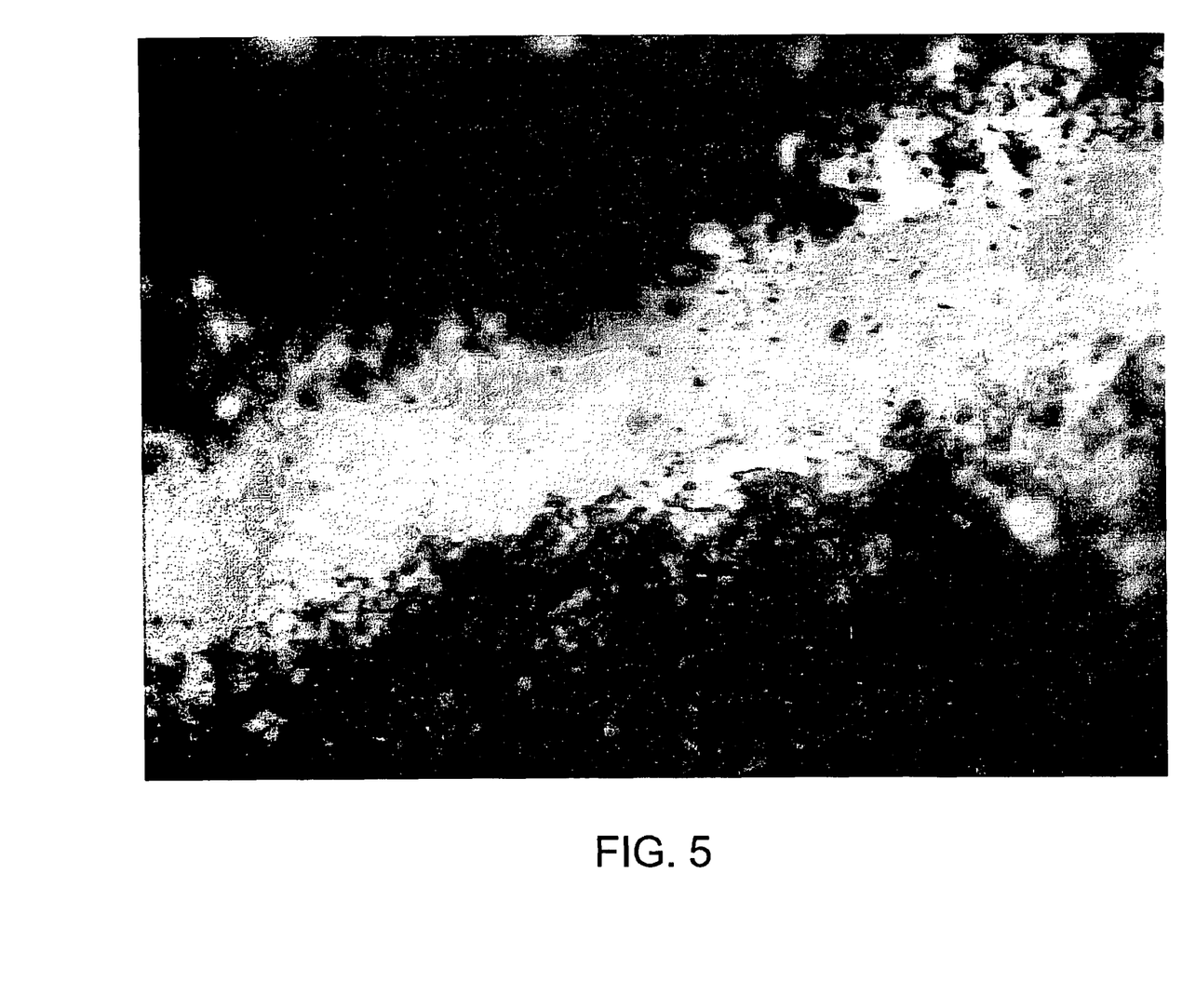
FIG. 5 is a photograph of a porous substrate with a layer of solids deposited thereon, after a sample has been taken by laser ablation.

Once solids comprising depleted MEA powder and internal standard material have been collected on the filter 650, the solids can be sampled and analyzed for catalytic element content. In the step 300, a sample of the solids is obtained by laser ablation. As shown in FIG. 5, a 213 nm laser can be used to ablate or remove a controlled sample of solids from the surface of the filter 650. Alternatively, the powder can be deposited on one side of the filter 650 and the laser ablation can be done from the opposite side of the filter such that the laser ablates a sample including the entire thickness of the filter 650 plus the layer of powder. By ablating a sample from the opposite side of the filter 650, the laser power is sufficiently attenuated that the layer of powder is not blown off the filter 650. A 266 nm laser can also be used to ablate a sample of solids from the surface of the filter 650.

Figure 6:
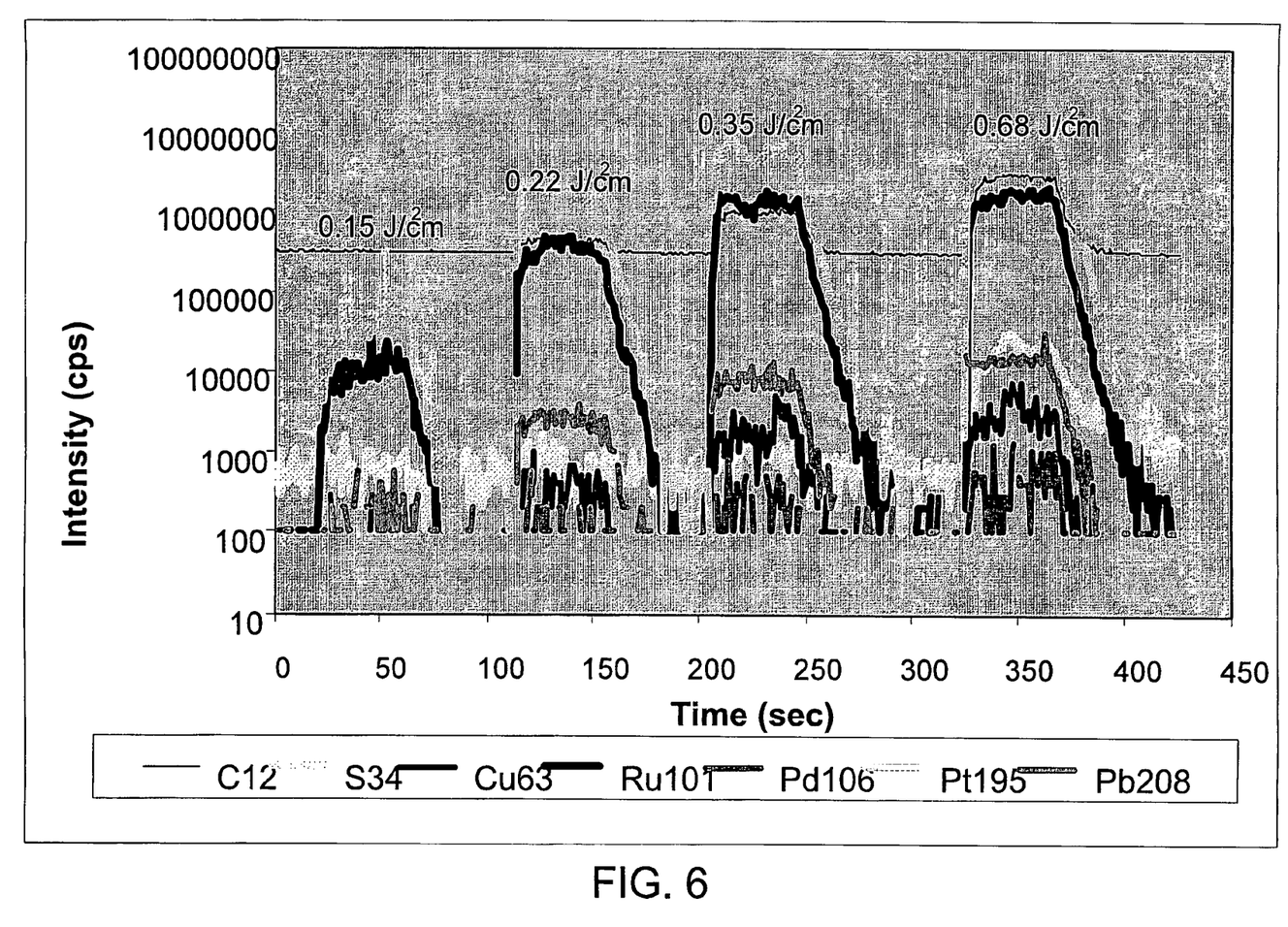
FIG. 6 is a graph showing the variation of intensity of mass spectrometer signals from platinum and other substances in the solids when the ablating laser power is varied.

The presence of the internal standard material in an intimate mixture with the depleted MEA powder enables the measured catalytic element content to be normalized to account for variations in sample size. Laser ablation creates an aerosol sample of powder that is transported in a carrier gas to an inductively coupled plasma torch for vaporization. Helium and argon are the most common carrier gases because of their compatibility with the inductively coupled plasma. Testing has shown that for the laser device used, variations in laser power can impact the measured concentration of catalytic element, as shown in the mass spectrometry measurements of FIG. 6. For example, a power level of at least about 0.15 Joules/cm$^2$ must be used to ablate a sufficient amount of sample, and increasing the power to above about 0.22 Joules/ cm$^2$ enables ablation of a sample extending essentially through the thickness of the layer of solids deposited on the filter. Increasing the power to about 0.35 Joules/cm$^2$ resulted in further signal improvement, but increasing the power further to 0.68 Joules/cm$^2$ resulted in minimal improved signal levels of catalytic element (platinum and ruthenium) in the analyzed samples. It is recognized that the laser power levels required for sampling are dependent on various factors, including but not limited to the spot size of the laser and the thickness of the solids layer on the filter.

Under some conditions, applying laser ablation to the solids deposited on the porous substrate can tend to blast the sample off the surface, due to the high energy of the laser beam. To ameliorate this problem, a fixing layer can be applied over the powder sample on the porous substrate. In one embodiment, an overcoat of acrylic lacquer can be sprayed over the powder layer on the substrate, as long as the lacquer does not contain any compounds that will interfere with the catalytic element and internal standard measurement techniques. For example, some lacquers contain carbon. In another embodiment, a sheet of aluminum foil can be placed over the powder layer on the substrate. Alternatively, the sample can be laser ablated from the opposite side of the filter from which the solids layer has been deposited.

In the step 400, the laser-ablated aerosol particles of the sample are fluidized in a carrier gas and vaporized using an inductively coupled plasma. The high temperature inductively coupled plasma causes the catalytic element and the internal standard material to be heated into the vapor phase. In the step 500, the concentration of catalytic element in the sample is determined by quantifying the intensity of a first signal correlated to the amount of catalytic element in the sample, quantifying the intensity of a second signal correlated to the amount of internal material in the sample, and normalizing the first signal by the second signal to account for variations in sample size.

Figure 7:
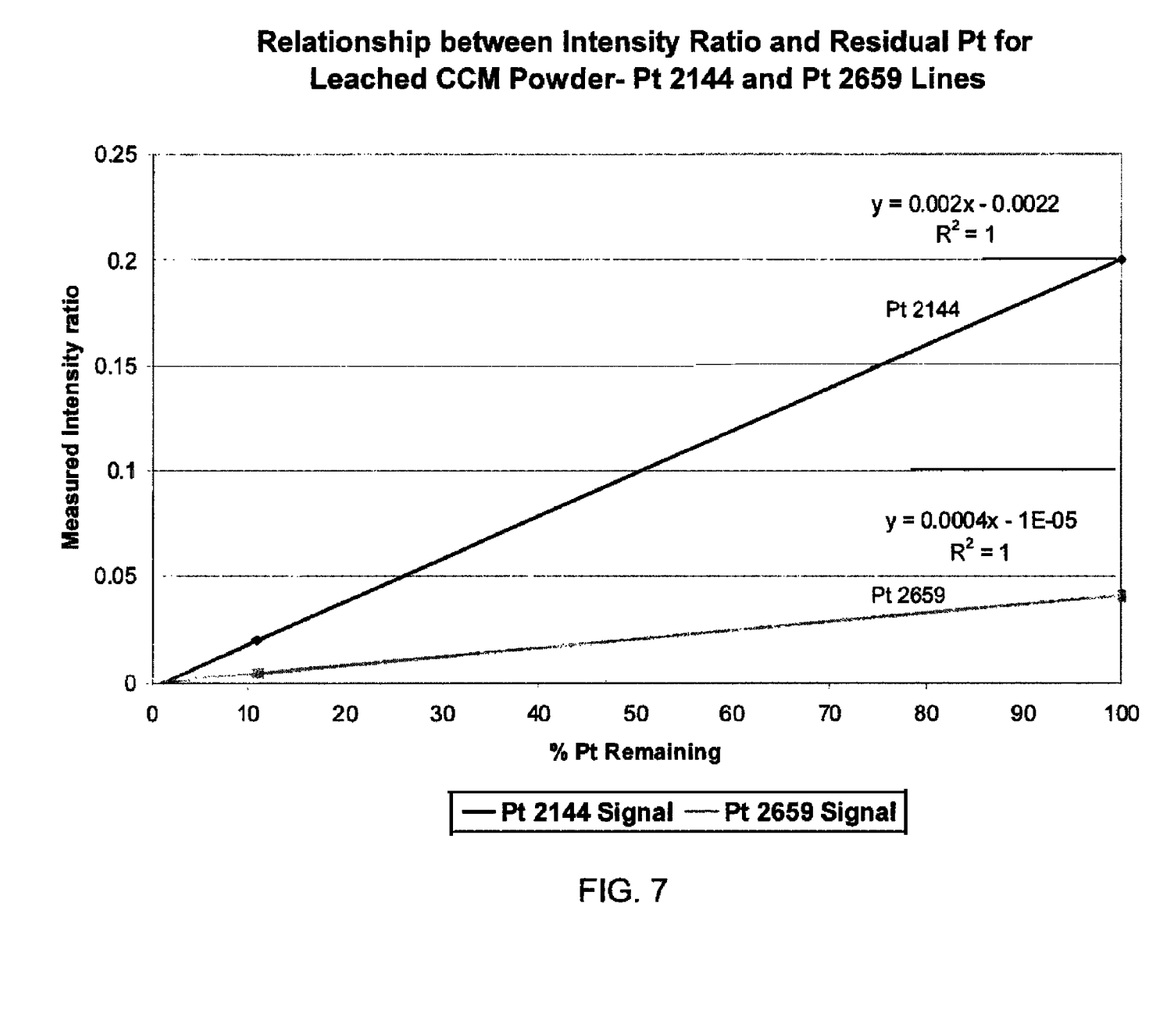
FIG. 7 is a graph showing a correlation between platinum concentration and measured optical emissions at characteristic wavelengths of platinum.

The first signal and second signal are determined by a measurement technique. In one embodiment, the measurement technique is optical emission spectroscopy, in which the characteristic light wavelengths emitted by the catalytic element and internal standard material in the plasma are detected and quantified. For example, excited platinum atoms emit light at several characteristic wavelength bands, including 214.4 nm and 265.9 nm. In another embodiment, the measurement technique is mass spectrometry, in which the concentration of catalytic element and internal standard material ions can be measured. A correlation between platinum concentration and optical emissions at characteristic wavelengths for platinum is shown in FIG. 7. Mass spectrometry is much more sensitive than optical emission spectroscopy, and is therefore useful in situations when only a small sample can be obtained or when catalytic element concentration in the depleted powder is very low. In yet another embodiment, X-ray fluorescence can be used to measure catalytic element concentration, but the variable composition and low average mass value of the MEA powder impacts the transmission of X-rays, which can cause variations in the catalytic element concentration measurements.

Although an internal standard is not required to determine the residual catalytic element concentration in a sample of depleted MEA powder, the purpose of the internal standard material is to normalize the intensity of the signal detected from the catalytic element to account for variations in sample size. Without an internal standard, the amount of catalytic element measured will be directly proportional to the amount of sample ablated by the laser, since the catalytic element is substantially uniformly dispersed in the sample. The size of a sample may vary due to several factors, including but not limited to the power of the laser used to ablate the sample (i.e., the laser penetration into the solids layer on the porous substrate), the width of the laser beam, the duration of application of the laser, the thickness of the solids layer or layers collected on the filter (i.e., the total amount of solids in the MEA powder slurry), and the uniformity of dispersion of the solids layer across the filter. However, by using an internal standard material that is intimately and reproducibly mixed with the MEA powder in the solids that are collected on the filter, variations in these and other parameters can be accommodated. In one embodiment, the internal standard material is in the form of a finely divided refractory powder that is substantially uniformly dispersed in the sample. By quantifying the intensity of a signal corresponding to the amount of catalytic element in the sample and another signal corresponding to the amount of internal standard material in the sample, a normalized measurement of the catalytic element concentration can be determined based on a ratio between the two signals, canceling out the effects of sample size.

Various substances can be used as the internal standard material. The internal standard material can be an element detectable in the plasma or a compound containing such an element. In one example, an element contained in the MEA powder, such as carbon, can be used as an internal standard, provided that the porous substrate does not also contain carbon, since any carbon vaporized from the porous substrate could potentially distort the measurement of the internal standard material in the powder. In another example, sulfur, an element present in the sulfonated perfluoropolymer membrane of the MEA, can be used as an internal standard, again provided that the porous substrate does not also contain sulfur. In still another embodiment, a compound of the porous substrate itself can be used as an internal standard. For example, a porous substrate made from glass microfibers would contribute elemental silicon vapor to the sample as an internal standard material, either when the laser ablation is sufficiently powerful and repeatable to cut all the way through the solids layer or layers and ablate a controlled amount of the porous substrate material or when a sample is taken by laser ablation through the porous substrate material.

In yet another embodiment, an acid-insoluble element not present in the MEA powder such as titanium (Ti), magnesium (Mg), aluminum (Al), silicon (Si), or zirconium (Zr) can be used as the internal standard material. For example, Ti can be provided in the form of rutile (TiO$_2$, titanium dioxide, a refractory), Mg and Si can be provided in the form of steatite (3MgO·4SiO$_2$·4H$_2$O, hydrated magnesium silicate), Al can be provided in the form of α-alumina (Al$_2$O$_3$, a refractory), Zr can be provided in the form of zirconium dioxide (ZrO$_2$), and Zr and Si can be provided in the form of ZrSiO$_4$ (zirconium silicate). These, and other similar elements, are not normally present in a fuel cell MEA and thus do not interfere with the measurement of platinum (Pt). Additionally, both Ti and Mg have a sensitivity of about one order of magnitude greater than Pt when measured by optical emission spectroscopy, after having been vaporized in an inductively coupled plasma, so that either can be used as an internal standard at a relatively low concentration compared with the Pt concentration. By mixing a known predetermined concentration of internal standard material into the slurry mixture, and then measuring the intensity of the signal correlated with the corresponding internal standard element in the sample, an absolute concentration of Pt in the sample can be determined.

To further increase the accuracy of the determination of residual catalytic element in the depleted MEA powder, the MEA powder can be sampled both before and after leaching.

In particular, a slurry of MEA powder and surfactant can first be created and sampled using any of the techniques discussed above, leachate is added to leach catalytic element from the MEA powder, and the resultant slurry is be sampled to measure the amount of catalytic element not extracted by the leachate. The ratio of the catalytic element measured in the pre-leach and post-leach samples can be taken to determine the net catalytic element recovery.

The use of an internal standard, in combination with catalytic element measurements, has been shown to improve the reproducibility of the residual catalytic element determination and compensates for disuniformities in solids dispersion on the porous substrate and variations in sample size obtained by laser ablation. Exemplary measurements are as follows. As a baseline for comparing different internal standards, a well-mixed slurry or suspension of aluminum oxide was combined with a well-mixed slurry or suspension of steatite in a mixing valve to form a substantially uniform mixture, and the mixture was deposited on a 25 mm diameter glass fiber filter mounted in a syringe filter holder. The mixture has about 5% aluminum oxide solids and about 0.5% steatite solids, for a ratio of about 10:1 in concentrations. Experiments were conducted, each consisting of twenty-five sets of five-second integrations, in which Al and Mg concentrations were measured and the results averaged. The aggregated results of 13 experiments show that the raw Al counts measured by optical emissions ranged almost a full order of magnitude, from 167/sec to 1459/sec, with a relative standard deviation of 43% (i.e., the standard deviation is 43% of the mean). However, by normalizing the Al measurements with Mg measurements from the same samples, the normalized Al/Mg counts ranged from 1.00 to 1.40, with a relative standard deviation of only about 10% and a reduction in variance of about 92%. Thus, using Mg as an internal standard to normalize Al data greatly improved the accuracy of Al measurements.

Similar results were obtained using Pt measurement data with steatite as an internal standard material. Two experiments were conducted, first sampling as received MEA powder with internal standard followed by sampling of MEA powder that had been leached and then mixed with internal standard. In both cases the internal standard was intermixed with the MEA powder using the online technique discussed above. The MEA powder was mixed with water to make a 5% weight/weight suspension, while the steatite was mixed with water to make a 0.5% weight/weight suspension. For both experiments, Pt was measured at two characteristic emission wavelengths (214.4 nm and 265.9 nm) and Si was measured at two characteristic emission wavelengths (212.4 nm and 251.6 nm), to factor out any difference in emission detection. Rather than using an adhesive to keep the MEA powder in place on a glass fiber filter, the filtration was performed with a polymer filter and the laser ablation was performed through the back of the filter. By switching from a glass filter to one made with a polymer, silicon could be used in place of magnesium as the internal standard.

In the first experiment, the laser power was set to 100%, the raster width set at 200 microns, the laser spot set at 350 microns and the laser movement set at 450 microns/sec. Eight sets of five-second integrations were conducted for each run, and the results averaged. Comparing the two sets of runs, the raw Pt data at 214.4 nm varied in the ratio of 1.32 (4384 counts to 3330 counts) and the raw Pt data at 265.9 nm varied in the ratio of 1.35 (4485 counts to 3316 counts). However, when normalized based on the Si measurements, the normalized ratio between experiments was 1.02 at 214.4 nm and 1.06 at 251.6 nm. The intensity ratio for Pt/Si was 0.206 at 214.4 nm and 0.042 for 265.9 nm.

The second experiment used 2.5 g of MEA powder that had been acid-leached. After leaching, the powder was first filtered to remove leachate and then washed to ensure that entrained Pt was removed. Analysis of the filtrate determined that 89% of the Pt was removed by the leaching process. The MEA powder was then re-slurried and sampled using the above-mentioned internal standard addition method. In this test, the power was set at 80%, the raster width set to 200 microns, the laser spot size set at 350 microns and the laser movement rate set at 250 microns/sec. Nine sets of runs with ten repeats each were performed. Under these conditions, the ratio of the high/low range of Pt to the internal standard was 1.47 and 1.43, for Pt 214.4 nm and Pt 265.9 nm, respectively. By contrast, the ratio of the high/low ranges of raw Pt counts were 3.95 and 3.23 for the same wavelengths. Similarly, the relative standard deviation for the ratioed signal was 16% at both wavelengths, but the uncorrected Pt signal had a relative standard deviation of 48.7% and 44.1% for Pt 214.4 nm and Pt 265.9 nm, respectively. For the depleted sample, intensity ratios of 0.0219 and 0.0048 were calculated for the two respective Pt wavelengths. The intensity ratio data was plotted for the unleached and depleted MEA powders using a two-point fit, as shown in FIG. 7. The intercept for both lines had less than 1% deviation from the origin based on the data, indicating that the method linearity can be extrapolated to fully depleted samples.

While the invention has been disclosed with reference to certain preferred embodiments, numerous modifications, alterations, and changes to the described embodiments are possible without departing from the sphere and scope of the invention, as defined in the appended claims and equivalents thereof. Accordingly, it is intended that the invention not be limited to the described embodiments, but that it have the full scope defined by the language of the following claims.

We claim:

1. A method for measuring the concentration of a catalytic element in a powder containing no more than about 2 percent of the catalytic element by weight, comprising:
    depositing on an outer surface of a porous substrate at least one layer of a powder mixture comprising the powder and an internal standard material;
    ablating a sample of the powder mixture deposited in the at least one layer using a laser;
    vaporizing the sample using an inductively coupled plasma;
    quantifying the intensity of a first signal correlated to the amount of catalytic element in the sample;
    quantifying the intensity of a second signal correlated to the amount of internal standard material in the sample; and
    determining a normalized concentration of catalytic element in the sample based on the ratio of the first signal intensity to the second signal intensity.

2. The method of claim 1, wherein the powder is a fuel cell powder.

3. The method of claim 1, wherein the catalytic element is selected from the group consisting of platinum, ruthenium, palladium, gold, and rhodium.

4. The method of claim 1, wherein the internal standard material contains a predetermined concentration of an inorganic element absent from the powder, the material being insoluble in acid.

5. The method of claim 4, wherein the inorganic element is selected from the group consisting of titanium, magnesium, aluminum, silicon, and zirconium.

6. The method of claim 4, wherein the internal standard material comprises a finely divided refractory powder.

7. The method of claim 1, wherein the internal standard material contains a predetermined concentration of titanium in the form of rutile.

8. The method of claim 1, wherein the internal standard material contains a predetermined concentration of magnesium and silicon in the form of steatite.

9. The method of claim 1, wherein the step of depositing a layer of powder mixture on an outer surface of a porous substrate comprises:
   forming a first slurry comprising the powder;
   forming a second slurry comprising the internal standard material;
   mixing the first slurry and the second slurry into a substantially uniform slurry mixture having a liquid portion and a solids portion; and
   exposing the slurry mixture to the porous substrate so that the liquid portion passes through the porous substrate and the solids portion is deposited on the outer surface of the porous substrate to form the layer of powder mixture.

10. The method of claim 9, wherein the first slurry further comprises a leachate.

11. The method of claim 9, wherein the first slurry further comprises a surfactant.

12. The method of claim 9, wherein the porous substrate is a syringe filter and wherein the powder and the internal standard material are deposited on the filter with a substantially identical degree of variability.

13. The method of claim 1, wherein prior to the step of ablating the powder mixture, the method further comprises applying a fixing layer on top of the layer of powder mixture to retain the layer of powder mixture intact during laser ablation.

14. The method of claim 13, wherein the fixing layer comprises one of an acrylic lacquer film and a sheet of aluminum foil.

15. The method of claim 1, wherein the layer of powder mixture is deposited on one side of the porous substrate and wherein the sample is ablated by a laser through the opposite side of the porous substrate.

16. The method of claim 1, wherein quantifying the intensity of the first signal comprises optical emission spectroscopy to detect emission of light from the vaporized sample at one or more characteristic wavelengths of the catalytic element and wherein quantifying the intensity of the second signal comprises optical emission spectroscopy to detect emission of light from the vaporized sample at one or more characteristic wavelengths of the internal standard material.

17. The method of claim 1, wherein quantifying the intensity of the first signal and quantifying the intensity of the second signal comprises mass spectrometry.

18. A method for measuring, the recovery of a catalytic element from a fuel cell membrane electrode assembly powder containing no more than about 2 percent of the catalytic element, the method comprising:
   depositing on an outer surface of a porous substrate a layer of a first powder mixture comprising the fuel cell powder;
   ablating a first sample of the first powder mixture deposited in the layer of the first powder mixture using a laser;
   vaporizing the first sample using an inductively coupled plasma;
   determining the concentration of catalytic element in the first sample;
   extracting at least a portion of the catalytic element from the fuel cell powder to create a depleted fuel cell powder;
   depositing on an outer surface of a porous substrate a layer of a second powder mixture comprising the depleted fuel cell powder;
   ablating a second sample of the second powder mixture deposited in the layer of the second powder mixture using a laser;
   vaporizing the second sample using an inductively coupled plasma; and
   determining the concentration of catalytic element in the second sample.

19. The method of claim 18, wherein the steps of depositing a first and second layer of powder mixture on an outer surface of a porous substrate each comprises:
   forming a slurry comprising a substantially uniform mixture of the fuel cell powder and an internal standard material, the slurry having a solids portion and a liquid portion;
   exposing the slurry mixture to the porous substrate so that the liquid portion passes through the porous substrate while the solids portion is deposited on the other surface of the porous substrate to form the layer of powder mixture comprising the fuel cell powder and the internal standard material.

20. The method of claim 19, wherein the step of determining the catalytic element in the sample comprises;
   measuring the intensity of a first signal correlated to the amount of catalytic element by detecting the optical emission from the vaporized sample at one or more characteristic wavelengths for the catalytic element;
   measuring the intensity of a second signal correlated to the amount of internal standard material by detecting the optical emission from the vaporized sample at one or more characteristic wavelengths for the internal standard material; and
   calculating a normalized concentration of the catalytic element in the sample based on the ratio of the first signal intensity to the second signal intensity.

21. The method of claim 20, wherein the internal standard material comprises an element selected from the group consisting of titanium, magnesium, aluminum, silicon, and zirconium.

* * * * *